US010905311B2

(12) United States Patent
Nakagawa

(10) Patent No.: US 10,905,311 B2
(45) Date of Patent: Feb. 2, 2021

(54) OPTICAL MODULE FOR ENDOSCOPE, ENDOSCOPE, AND MANUFACTURING METHOD FOR OPTICAL MODULE FOR ENDOSCOPE

(71) Applicant: OLYMPUS CORPORATION, Tokyo (JP)

(72) Inventor: Yusuke Nakagawa, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/793,383

(22) Filed: Feb. 18, 2020

(65) Prior Publication Data

US 2020/0178761 A1 Jun. 11, 2020

Related U.S. Application Data

(63) Continuation of application No. PCT/JP2017/030635, filed on Aug. 25, 2017.

(51) Int. Cl.

*A61B 1/07* (2006.01)
*A61B 1/018* (2006.01)
*G02B 23/24* (2006.01)
*A61B 1/00* (2006.01)

(52) U.S. Cl.

CPC ........ *A61B 1/0011* (2013.01); *A61B 1/00126* (2013.01); *A61B 1/018* (2013.01); *A61B 1/07* (2013.01); *G02B 23/2415* (2013.01); *G02B 23/2423* (2013.01); *G02B 23/2469* (2013.01); *G02B 23/2484* (2013.01)

(58) Field of Classification Search

CPC .............. A61B 1/0011; A61B 1/00126; G02B 23/2415; G02B 23/2423

See application file for complete search history.

(56) References Cited

U.S. PATENT DOCUMENTS 6,917,745 B2 * 7/2005 Murata .................. B29D 11/00 385/137
2004/0247259 A1 * 12/2004 Blom .................. G02B 6/4292 385/92
2007/0189676 A1 8/2007 Nagasaka
(Continued)

FOREIGN PATENT DOCUMENTS

CN 1548938 A 11/2004
JP 2005-292739 A 10/2005
(Continued)

OTHER PUBLICATIONS

International Search Report dated Nov. 7, 2017 issued in PCT/JP2017/030635.

*Primary Examiner* — Sung H Pak

(74) *Attorney, Agent, or Firm* — Scully, Scott, Murphy Presser, P.C.

(57) ABSTRACT

An optical module for endoscope includes an optical element including an external terminal, a housing in which an insertion hole into which an optical fiber is inserted is present and has a bottom and a bottom surface made of a transparent material, and a sealing plate that is bonded to the housing. The optical element is stored in an upper recess of the housing, the external terminal and a bonding electrode are connected using a bonding wire, and a wire recess in which a part of the bonding wire is stored is present in a bottom surface of the upper recess.

11 Claims, 9 Drawing Sheets

O
10
30SA
1A
31A
30A
20SA
H31
H32A
32A
32B
29
40SA
48A
40A
50
46A
S20
20SB
20A
45
Z
Y
X

(56) References Cited

U.S. PATENT DOCUMENTS

| | | | | |
|---|---|---|---|---|
| 2014/0270650 | A1* | 9/2014 | Kasten | G02B 6/4292 385/78 |
| 2015/0086162 | A1* | 3/2015 | Miyahara | G02B 23/2446 385/33 |
| 2015/0098237 | A1* | 4/2015 | Motohara | G02B 6/423 362/554 |
| 2015/0342530 | A1 | 12/2015 | Dekker et al. | |

FOREIGN PATENT DOCUMENTS

| | | | |
|---|---|---|---|
| JP | 2005-353637 | A | 12/2005 |
| JP | 2007-206337 | A | 8/2007 |
| JP | 2012-160526 | A | 8/2012 |
| JP | 2015-087744 | A | 5/2015 |
| JP | 2015-524285 | A | 8/2015 |
| WO | WO 2014/006536 | A2 | 1/2014 |

* cited by examiner

OPTICAL MODULE FOR ENDOSCOPE, ENDOSCOPE, AND MANUFACTURING METHOD FOR OPTICAL MODULE FOR ENDOSCOPE

CROSS REFERENCE TO RELATED APPLICATION

This application is a continuation application of PCT/JP2017/030635 filed on Aug. 25, 2017, the entire contents of which are incorporated herein by this reference.

BACKGROUND OF THE INVENTION

1. Field of the Invention

The present invention relates to an optical module for endoscope including a housing in which an insertion hole into which an optical fiber is inserted is present, a sealing plate bonded to the housing, and an optical element stored in a space formed by bonding the housing and the sealing plate using an annular bonding material, an endoscope including the optical module for endoscope, and a manufacturing method for the optical module for endoscope.

2. Description of the Related Art

The endoscope includes an image pickup apparatus including an image pickup device such as a CCD at a distal end portion of an elongated insertion portion. In recent years, use of the image pickup device including a large number of pixels in the endoscope has been examined. In the image pickup apparatus in which the image pickup device including a large number of pixels is used, an amount of signals transmitted from the image pickup device to a signal processing apparatus increases. Therefore, optical signal transmission through an optical fiber by an optical signal is desirable instead of electric signal transmission through a metal wire by an electric signal. For the optical signal transmission, an E/O-type optical module (an electrooptical converter) that converts an electric signal into an optical signal and an O/E-type optical module (a photoelectric converter) that converts an optical signal into an electric signal are used.

Reduction in size of an optical module is important for reduction in a diameter of an insertion portion of the endoscope. Further, an optical element is desirably air-tightly sealed for improvement of reliability of the optical module.

Japanese Patent Application Laid-Open Publication Nos. 2005-292739 and 2012-160526 disclose an optical module in which an optical element is mounted on a substrate having translucency and is stored in a package in which a recess is present.

Japanese Patent Application Laid-Open Publication No. 2015-524285 discloses a medical device that inserts the optical fiber into an insertion hole, a bottom surface of which is made of oxide silicon and in which the optical element is mounted on a facing surface.

SUMMARY OF THE INVENTION

An optical module for endoscope according to an embodiment includes an optical element including a light emitting circuit configured to output an optical signal or a light receiving circuit to which the optical signal is inputted and an external terminal connected to the light emitting circuit or the light receiving circuit; a housing including a first principal plane and a second principal plane on an opposite side to the first principal plane, an insertion hole into which an optical fiber configured to transmit the optical signal is inserted being present, and an opening of the insertion hole that has a bottom and a bottom surface of which is made of a transparent material being present in the first principal plane; and a sealing plate including a third principal plane and a fourth principal plane on the opposite side to the third principal plane, the third principal plane being bonded to the second principal plane of the housing using an annular bonding material, wherein the optical element is stored in a space configured by an upper recess in which an opening is present in the second principal plane of the housing, and the optical element is arranged in the third principal plane, the external terminal and a bonding electrode in the third principal plane are connected using a bonding wire, and a wire recess in which a part of the bonding wire is stored is present in a bottom surface of the upper recess.

An endoscope according to another embodiment includes an optical module for endoscope, wherein the optical module for endoscope includes an optical element including a light emitting circuit configured to output an optical signal or a light receiving circuit to which the optical signal is inputted and an external terminal connected to the light emitting circuit or the light receiving circuit; a housing including a first principal plane and a second principal plane on an opposite side to the first principal plane, an insertion hole into which an optical fiber configured to transmit the optical signal is inserted being present, and an opening of the insertion hole that has a bottom and a bottom surface of which is made of a transparent material being present in the first principal plane; and a sealing plate including a third principal plane and a fourth principal plane on the opposite side to the third principal plane, the third principal plane being bonded to the second principal plane of the housing using an annular bonding material, wherein the optical element is stored in a space configured by an upper recess in which an opening is present in the second principal plane of the housing, and the optical element is arranged in the third principal plane, the external terminal and a bonding electrode in the third principal plane are connected using a bonding wire, and a wire recess in which a part of the bonding wire is stored is present in a bottom surface of the upper recess.

A manufacturing method for an optical module for endoscope according to still another embodiment includes bonding a first transparent wafer in which a wire recess is formed and a second transparent wafer in which a container recess is formed in a state in which the wire recess and the container recess are overlapped and manufacturing a bonding transparent wafer including an upper recess composed of the wire recess and the container recess; processing the first transparent wafer of the bonding transparent wafer into a thin layer; bonding a silicon wafer to the first transparent wafer of the bonding transparent wafer and manufacturing a bonding wafer; forming, by etching, an insertion hole in which an optical fiber is inserted into the silicon wafer of the bonding wafer; manufacturing a housing by cutting the bonding wafer; arranging, at a sealing plate, an optical element including a light emitting circuit that outputs an optical signal or a light receiving circuit in which the optical signal is inputted and an external terminal connected to the light emitting circuit or the light receiving circuit, and connecting the external terminal and a bonding electrode by a bonding wire; injecting a transparent resin into the upper recess; arranging glass frit that is a bonding material between the bonding wafer and the sealing plate in a state in which a part of the bonding wire is stored in the wire recess; and irradiating laser light onto the glass frit and bonding the bonding wafer and the sealing plate.

DETAILED DESCRIPTION OF THE PREFERRED EMBODIMENT(S)

First Embodiment

Figure 1:
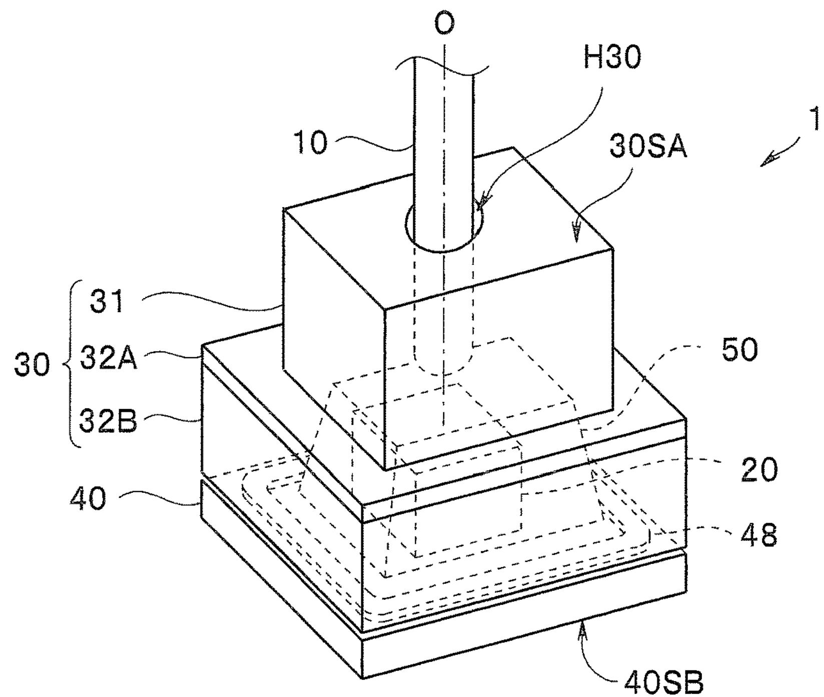
FIG. 1 is a perspective view of an optical module according to a first embodiment.

An optical module for endoscope 1 (hereinafter, referred to as an "optical module 1") according to a first embodiment will be described with reference to FIGS. 1 to 3. Note that, in the following description, drawings based on respective embodiments are schematic and relationships between thicknesses and widths of respective portions, ratios of the thicknesses of respective portions, and the like are different from actual ones. Portions having different mutual relationships and ratios of dimensions may be included among the drawings. Illustrations of a part of components and assigning of reference numerals and signs to a part of the components may be omitted. Further, an arrangement direction of an optical fiber 10, that is, a direction in which a value of a Z axis is increased in FIG. 1 etc., that is, an optical fiber arrangement direction is referred to as an "upper" direction.

An optical module 1 is an ultra-small E/O module (electrical-optical converter) that converts an electric signal outputted by an image pickup device of an endoscope 9 (see FIG. 18) to an optical signal and transmits the optical signal.

The optical module 1 includes, as a main component, an optical element 20, a housing 30 that is a fiber holding portion having a ferrule function, which holds the optical fiber 10, a sealing plate 40 that is a sealing portion bonded to the housing 30, and a bonding material 48 that is an annular bonding member bonding the housing 30 and the sealing plate 40.

The optical fiber 10 that transmits an optical signal includes a core that transmits an optical signal and a diameter of which is, for example, 50 μm and a clad that covers an outer periphery of the core and a diameter of which is 125 μm.

The optical element 20 is a VCSEL (Vertical Cavity Surface Emitting Laser) including a light emitting circuit 21 that is a light emitting portion outputting an optical signal. The ultra-small optical element 20, a dimension in plan view of which is 250 μm×250 μm and a height of which is 150 μm, includes the light emitting circuit 21, a diameter of which is 10 μm on a light emitting surface 20SA and two external terminals 22 that are connected to the light emitting circuit 21 and a diameter of which is 70 μm on the light emitting surface 20SA.

The housing 30 includes a first principal plane 30SA and a second principal plane 30SB on the opposite side to the first principal plane 30SA. The housing 30 has a function of a ferrule having an opening of an insertion hole H30 into which the optical fiber 10 is inserted on the first principal plane 30SA.

The housing 30 includes a ferrule 31 composed of silicon and a transparent portion composed of transparent containers 32A and 32B. A transparent container 32A is a transparent plate and a transparent container 32B is a storage portion. A bottom surface of the insertion hole H30 that penetrates the ferrule 31 is configured by the transparent container 32A that is a flat plate. In other words, the insertion hole H30 is a recess having a bottom. The transparent containers 32A and 32B have transparency with respect to light having a wavelength (850 to 1600 nm) of an optical signal. In addition, at the same time, the transparent containers 32A and 32B have transparency also with respect to laser for melting glass frit to be described later.

For example, the ultra-small housing 30, a dimension in plan view of which is 1000 μm×1000 μm, includes the ferrule 31 having a thickness of 350 μm, the transparent container 32A having a thickness of 30 μm, and the transparent container 32B having a thickness of 200 μm.

Note that, in the optical module 1, the ferrule 31 has the dimension in plan view of 500 μm×500 μm and the ferrule 31 is not arranged in an outer peripheral portion on an upper surface of the transparent container 32A. As described later, the reason is that in the optical module 1, heating is performed by laser irradiation from above in a manufacturing process.

The housing 30 includes an upper recess H32 configuring an air-tightly sealed space S20 in which the optical element 20 is stored. The upper recess H32 in which an opening is present in the second principal plane 30SB includes a wire recess H32A in the transparent container 32A and a container recess H32B in the transparent container 32B. Note that a wall surface of the upper recess H32 configuring the space S20 is inclined in a state in which a cross section of a space decreases in size toward an upper direction (a direction of the insertion hole). Therefore, it is easy to insert the optical element 20 into the space S20.

The sealing plate 40 includes a third principal plane 40SA and a fourth principal plane 40SB on the opposite side to the third principal plane 40SA. Further, the third principal plane 40SA is bonded to the second principal plane 30SB of the housing 30 by using an annular bonding material 48. The sealing plate 40, in which the optical element 20 is arranged on the third principal plane 40SA, for example, is a ceramic wiring board. A bonding electrode 45 on the third principal plane 40SA of the sealing plate 40 is electrically connected to an external electrode 47 on the fourth principal plane 40SB via a through wiring 46.

An external terminal 22 on the light emitting surface 20SA of the optical element 20 and the bonding electrode 45 are electrically connected by using a bonding wire 29. The bonding wire 29 is bent slightly in an upper direction from a bonding portion between the bonding wire 29 and the external terminal 22, and then is connected to the bonding electrode 45 in a lower direction.

A part (upper part) of the bonding wire 29 is stored in the wire recess H32A of the transparent container 32A of the housing 30. In other words, the wire recess H32A in which a part of the bonding wire 29 is stored is present in a bottom surface (upper face) of the upper recess 32. Therefore, in the optical module 1, a distance between the light emitting circuit 21 (light emitting surface 20SA) of the optical element 20 and the transparent container 32A is shortened, a transmission efficiency of optical signals is increased, and a lower height of a length (a dimension in a Z direction) is facilitated.

The annular bonding material 48 that bonds the second principal plane 30SB of the housing 30 and the third principal plane 40SA of the sealing plate 40 is made of low-melting glass formed by heating glass frit by the laser irradiation.

Note, however, that components on the way in which laser light reaches the bonding material 48 are made of a material that is transparent and a melting point of which surpasses a melting point of the bonding material 48. For example, in a case in which the bonding material 48 is made of glass having a melting point of 400° C., in the transparent containers 32A and 32B, glass having a melting point of 500° C. or more, the melting point being higher than a melting point of the bonding material 48 by 50° C. or more, is desirably used.

On the other hand, the space S20 is filled with a transparent resin 50. The transparent resin 50 is a refractive index matching material, and at the same time, is also a reinforcing member that reinforces a mechanical strength of the thin transparent container 32A.

In other words, the transparent resin 50 that is filled between the light emitting circuit 21 of the optical element 20 and the transparent containers 32A and 32B has a function of the refractive index matching material. On the other hand, the transparent resin 50 that is arranged on the periphery of and on four side surfaces of the light emitting circuit 21 of the optical element 20 has a reinforcing effect of the transparent container 32A and an effect of reducing a stress that is applied to a bonding portion between the optical element 20 and the bonding wire.

A thickness of the transparent container 32A, that is, an optical path length of an optical signal in the transparent container 32A is as short as 30 μm, for example, so that 95% or more of light having a wavelength of an optical signal is transmitted. Therefore, when the optical fiber 10 is inserted into the insertion hole H30 in the housing 30, there is a possibility that the thin transparent container 32A is broken. However, as described later, in the optical module 1, the transparent container 32A is reinforced by the transparent resin 50 before inserting the optical fiber 10, and therefore the transparent container 32A is not broken.

Further, the space S20 in which the optical element 20 is stored is air-tightly sealed in order to improve reliability of the optical element 20. When a gas remains in the space S20, a thermal expansion coefficient of the gas is larger than a thermal expansion coefficient of a surrounding solid configuring the space S20. Therefore, since an internal gas is expanded/shrunk by an ambient temperature change, a stress is applied to the bonding portion of the bonding wire 29 and there is a possibility that bonding reliability is reduced.

However, since the space S20 is filled with the transparent resin 50, a remaining gas is small. Therefore, the bonding reliability of the optical element 20 is not reduced.

Further, in a conventional endoscope, when moisture is infiltrated to an optical module by an autoclave process in a high moisture environment or the like, deterioration in an optical element or peeling of sealing resins is caused and therefore there is a possibility that a light amount is changed.

However, the optical element 20 and the transparent resin 50 are air-tightly sealed by the glass frit made of inorganic materials having a low hygroscopic property and therefore the optical module 1 has a high humidity reliability and a light amount is stable.

As described above, the optical module 1 in which the space S20 in which the optical element 20 is stored is filled with the transparent resin 50 arranged in a state in which the light emitting circuit 21 of the optical element 20 is covered as the refractive index matching material has high reliability. In addition, since the transparent container 32A is not broken at the time of manufacturing, the optical module 1 has high productivity. Further, the optical element 20 that is air-tightly sealed by using the bonding material 48 made of annular glass has high reliability.

<Manufacturing Method for Optical Module>

Figure 4:
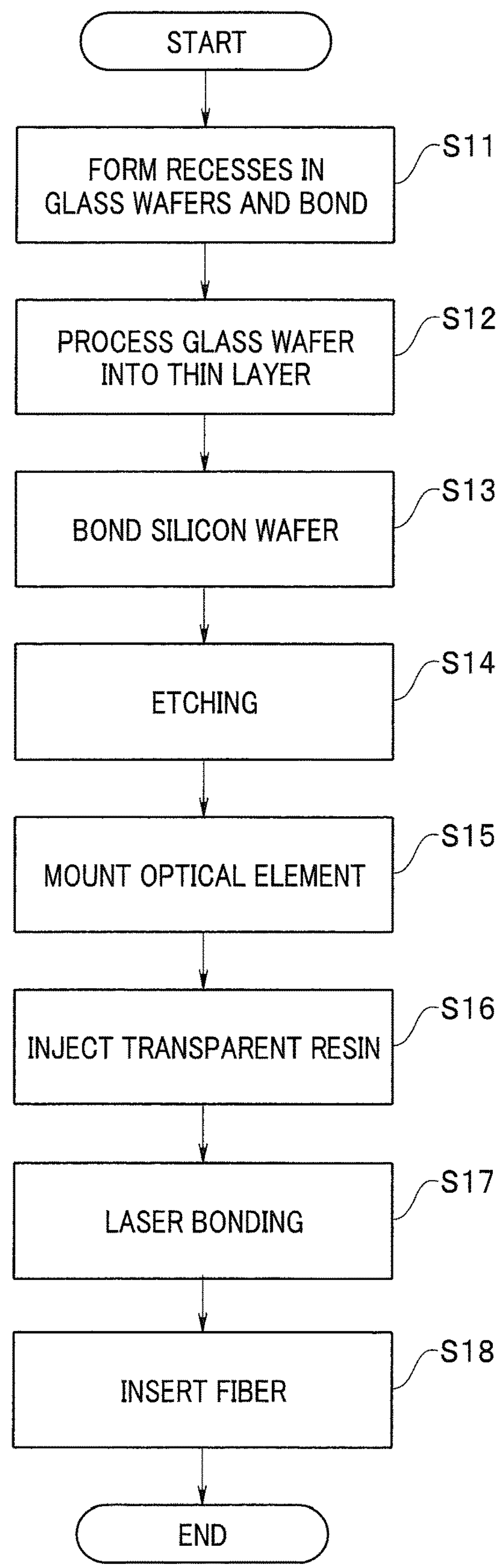
FIG. 4 is a manufacturing flowchart of the optical module according to the first embodiment.

A manufacturing method for the optical module will be described with reference to a flowchart shown in FIG. 4. A main structure is manufactured in a wafer state and then the optical module 1 is individualized.

<Step S11> Formation/Bonding of Recess in/to Transparent Wafer

Figure 5:
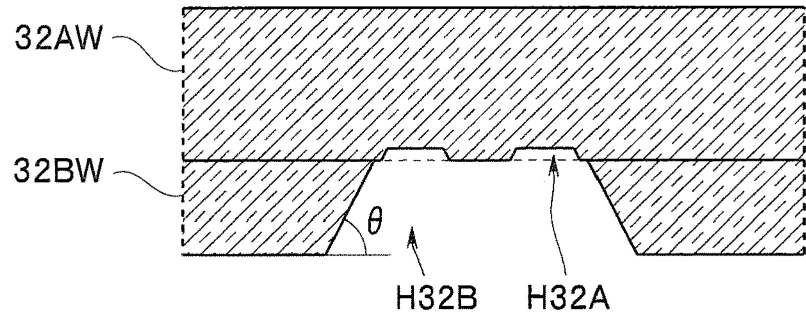
FIG. 5 is a cross-sectional view describing a manufacturing method for the optical module according to the first embodiment.

As shown in FIG. 5, after the wire recess H32A and the container recess H32B that is a space are formed, both of the first transparent wafer 32AW and the second transparent wafer 32BW are bonded, respectively, for example, by using an anodic bonding method. More specifically, the first transparent wafer 32AW in which the wire recess H32A is formed and the second transparent wafer 32BW in which the container recess H32B is formed are bonded in a state in which the wire recess H32A and the container recess H32B are overlapped. Further, the bonding transparent wafer including the upper recess H32 formed by the wire recess H32A and the container recess H32B is manufactured.

A wall surface of the recess formed by a sand blaster process having high productivity is an inclined plane having an inclination angle θ of 60 to 70 degrees. In other words, it is easy to produce a recess, a wall surface of which is inclined.

The first transparent wafer and the second transparent wafer are constituted by glass or the like that is a substantially transparent material with respect to a wavelength of light of optical signals. In a case in which light of optical signals is infrared light, a transparent wafer may be constituted by silicon that does not transmit visible light but transmit infrared light, for example.

<Step S12> Processing of Transparent Wafer into Thin Layer

Figure 6:
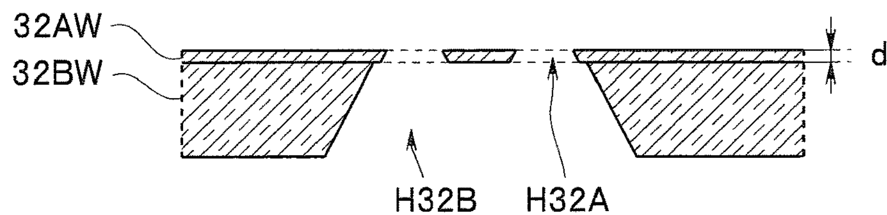
FIG. 6 is a cross-sectional view describing a manufacturing method for the optical module according to the first embodiment.

As shown in FIG. 6, the first transparent wafer 32AW is processed into a thin layer, until a thickness of 30 μm is obtained, for example. In order to improve the transmission efficiency, it is desirable that a thickness d of the first transparent wafer 32AW is 50 μm or less, which transmits 95% or more of light of wavelength of optical signals. Note that when the thickness d of the transparent wafer 32AW is, for example, 5 μm or more, there is no possibility that breakage is caused in a process until step 17 to be described later.

<Step S13> Bonding of Silicon Wafer

Figure 7:
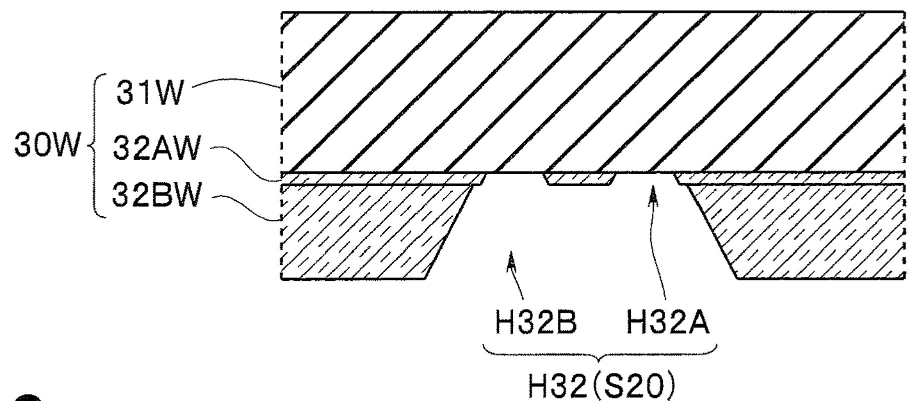
FIG. 7 is a cross-sectional view describing a manufacturing method for the optical module according to the first embodiment.

As shown in FIG. 7, a silicon wafer 31W is, for example, anodically bonded to the first transparent wafer 32AW of the bonding transparent wafer to manufacture a bonding wafer 30W. The wire recess H32A and the container recess H32B are the upper recess H32 configuring the space S20.

<Step S14> Etching

Figure 8:
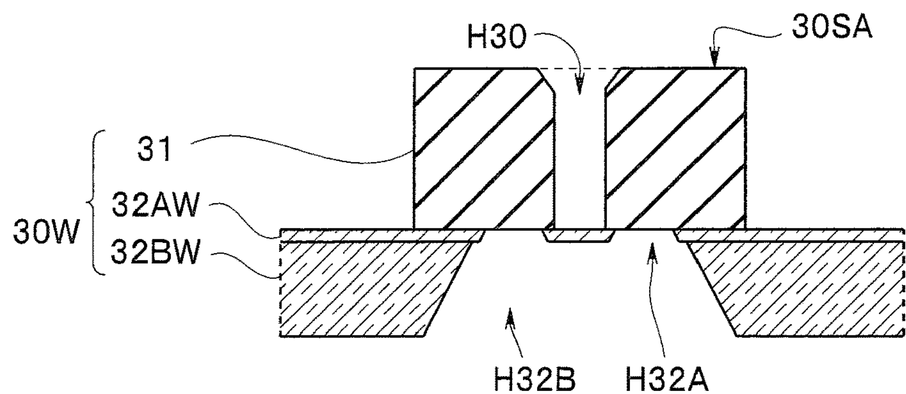
FIG. 8 is a cross-sectional view describing a manufacturing method for the optical module according to the first embodiment.

As shown in FIG. 8, an etching mask is arranged on the first principal plane 30SA of the silicon wafer 31W and then dry etching processing such as RIE is performed. Further, the transparent wafer 32AW becomes an etching stop layer and the insertion hole H30 that penetrates the silicon wafer 31W is formed. In a case in which an outer diameter of the optical fiber 10 is 125 μm, for example, the insertion hole H30 having an inner diameter of 132 μm is formed.

The insertion hole H30 may be formed by wet etching. In addition to a column shape, when the optical fiber 10 can be held in an inner surface, the insertion hole H30 may be a prismatic shape. Further, the insertion hole H30 may have a tapered shape in which a diameter of an opening is larger than a diameter of the bottom surface.

Further, the insertion hole H30 is formed, and at the same time, the silicon wafer 31W is etched in a state of leaving the periphery of the insertion hole 1130, and thereby a plurality of ferrules 31 are manufactured.

The bonding wafer 30W is cut to thereby manufacture a plurality of housings 30.

<Step S15> Mounting of Optical Element

Figure 9:
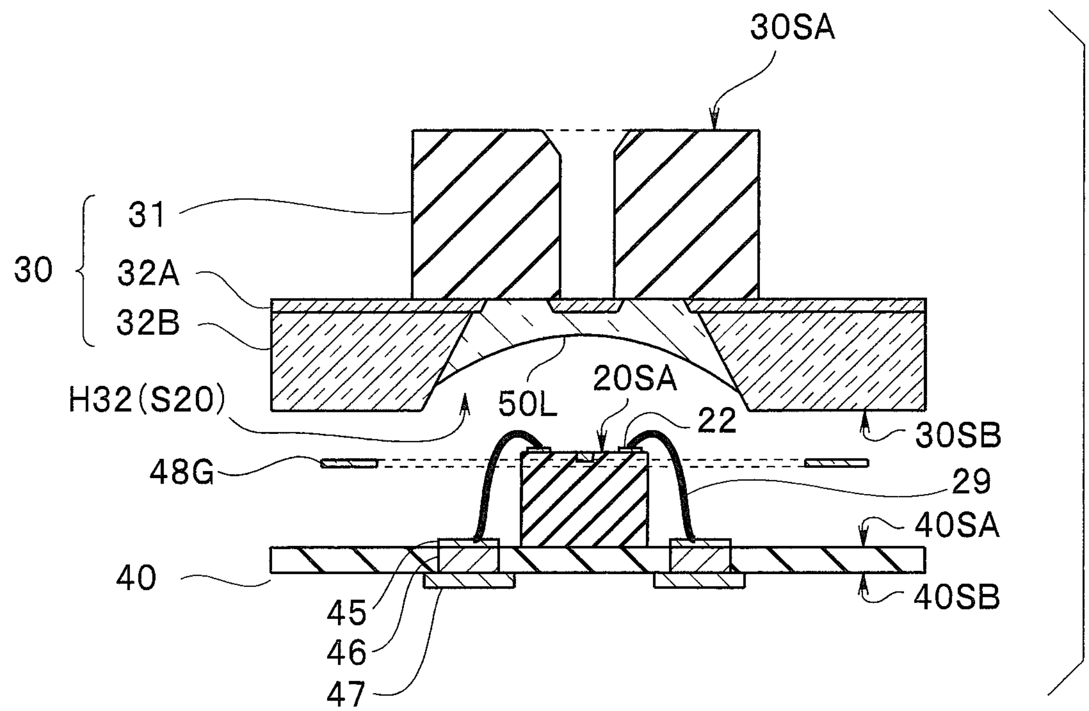
FIG. 9 is a cross-sectional view describing a manufacturing method for the optical module according to the first embodiment.

As shown in FIG. 9, the optical element 20 is fixed onto the third principal plane 40SA of the sealing plate 40 that is also a wiring board. Further, the external terminal 22 of the optical element 20 and the bonding electrode 45 on the third principal plane 40SA of the sealing plate 40 are electrically connected through the bonding wire 29 by using a wire bonding apparatus. The bonding wire 29 is a thin line made of gold, aluminum, or the like.

In the wire bonding, to obtain a stable bonding strength, the bonding wire 29 is drawn out in the upper direction from the bonding portion between the bonding wire 29 and the external terminal 22. The bonding wire 29 projects from the light emitting surface 20SA, for example, by 50 to 100 μm.

<Step S16> Injection of Transparent Resin

On the other hand, a liquid transparent resin 50L that is not cured is injected to the upper recess 1132 in the housing 30. An amount of the transparent resin 50L that is not cured is set by subtracting a volume of the optical element 20 from a volume of the upper recess H32 (space S20). As the transparent resin 50L, for example, a silicone resin or an epoxy resin is used among various resins having a predetermined refractive index in which an optical transparency is high.

Further, glass frit 48G that is annularly patterned is arranged between the second principal plane 30SB and the third principal plane 40SA. The glass frit 48G is, for example, powder of a low-melting glass having a melting point of 400° C.

<Step S17> Bonding of Laser

Figure 10:
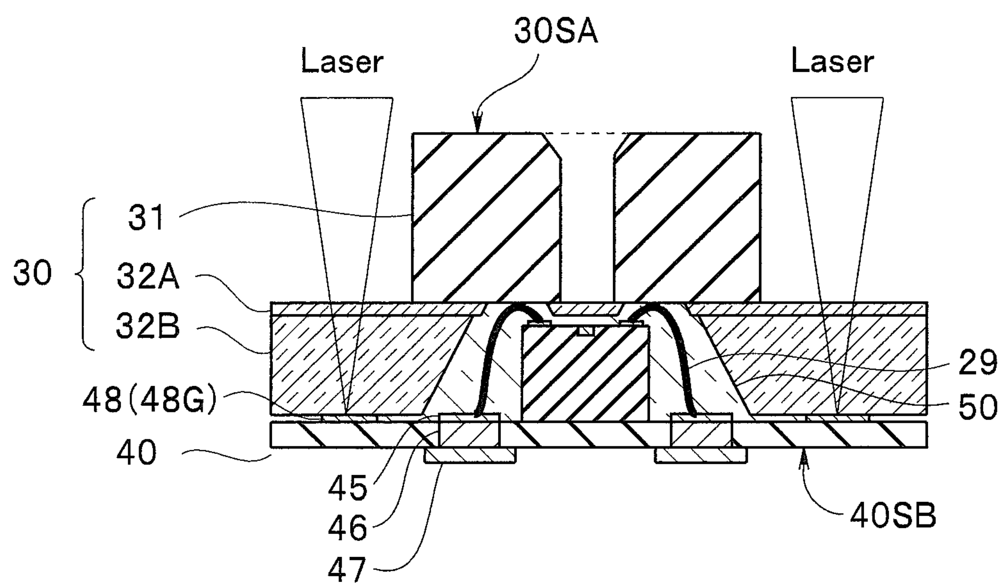
FIG. 10 is a cross-sectional view describing a manufacturing method for the optical module according to the first embodiment.

As shown in FIG. 10, when laser light is irradiated via the transparent containers 32A and 32B from above and is heated at a melting point or more, the glass frit 48G is brought into the bonding material 48 made of glass. A melting point of the transparent containers 32A and 32B is higher than a melting point of the bonding material 48. The ferrule 31 is made of silicon that intercepts laser light. However, the bonding material 48 is located around the ferrule 31 in plan view in a direction of the first principal plane 30SA.

The space S20 is air-tightly sealed by using the bonding material 48 made of glass.

<Step S18> Insertion of Fiber

Figure 2:
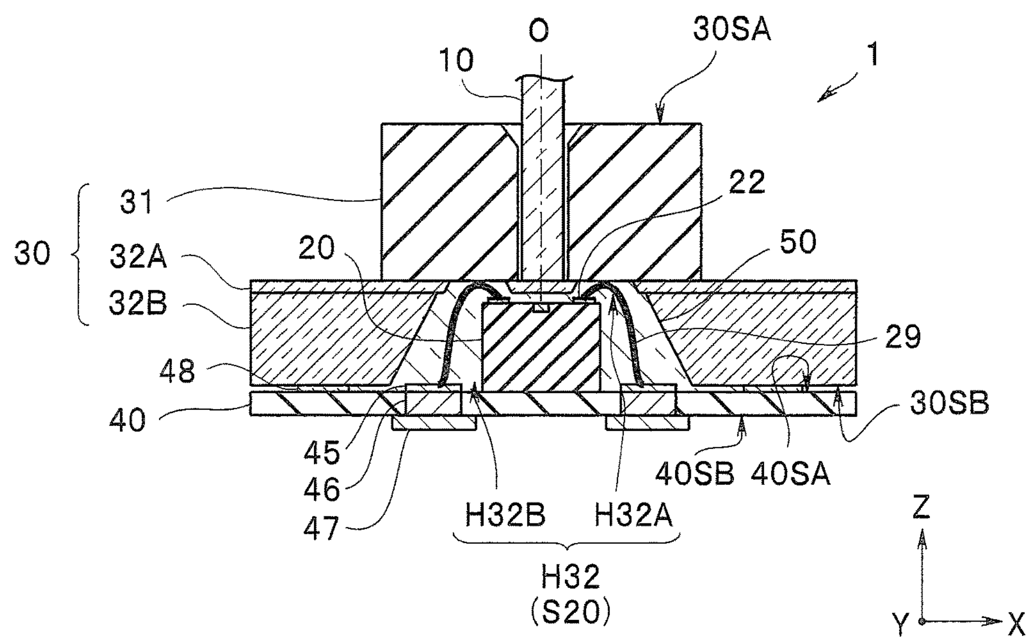
FIG. 2 is a cross-sectional view along a line II-II shown in FIG. 1 of the optical module according to the first embodiment.
Figure 3:
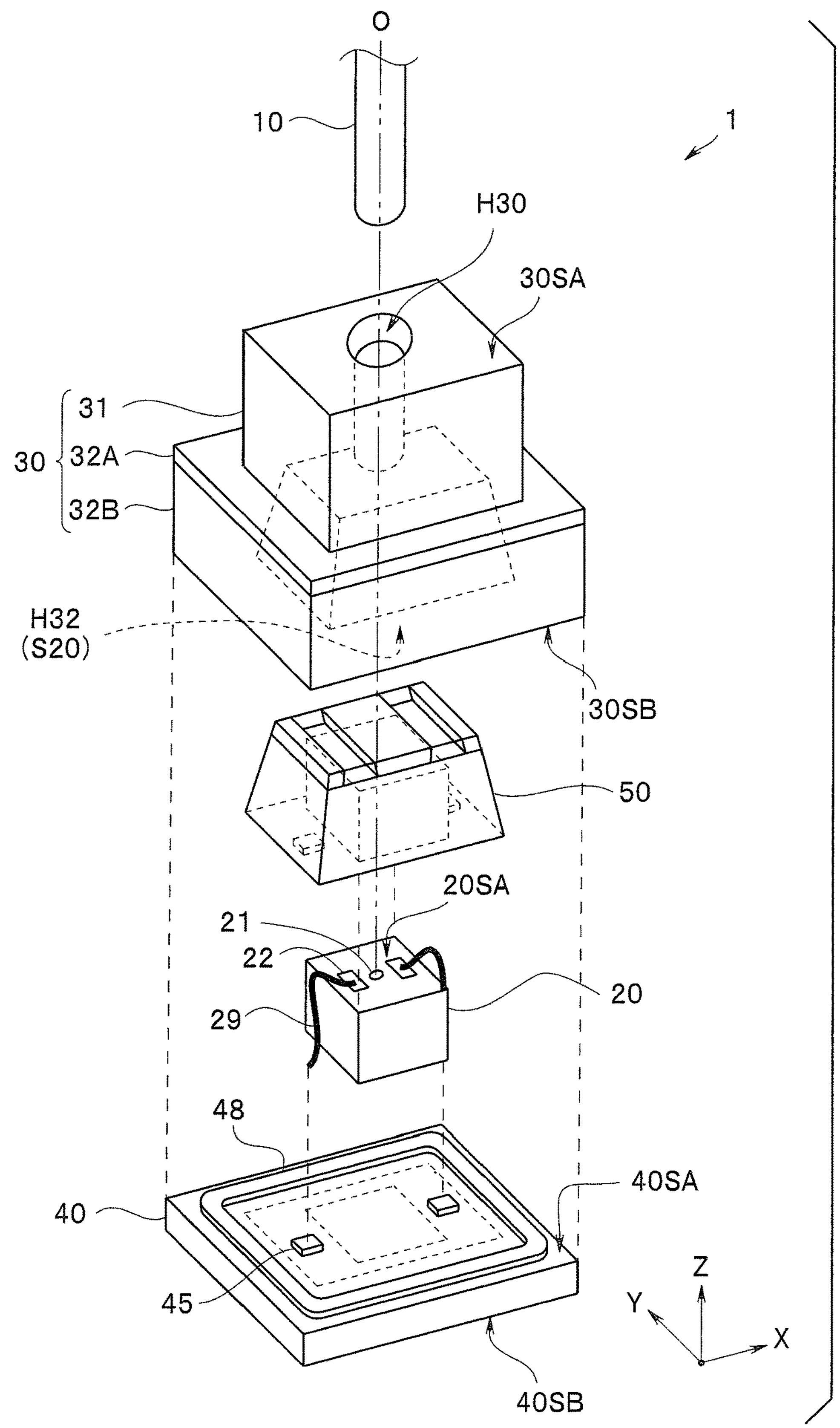
FIG. 3 is an exploded view of the optical module according to the first embodiment.

The optical fiber 10 is inserted into the insertion hole H30 and the optical module 1 shown in FIG. 2 is manufactured. The optical fiber 10 is arranged in a state in which a distal end surface of the optical fiber 10 abuts on a bottom surface of the insertion hole H30 and is fixed by using an adhesive agent (not shown). At this time, the optical fiber 10 comes into contact with the transparent container 32A configuring the bottom surface of the insertion hole H30.

A mechanical strength of the thin transparent container 32A is not sufficient. However, the transparent container 32A on the bottom surface side (optical element side) is reinforced by the transparent resin 50L. Therefore, the transparent container 32A is not broken even if the optical fiber 10 comes into contact with the transparent container 32A. Therefore, the optical module 1 has high productivity.

As described above, according to a manufacturing method for the optical module according to the present embodiment, the bonding material 48 is formed by heating the glass frit 48G by using the laser irradiation. The optical element 20 that is stored in the space S20 air-tightly sealed by the bonding material 48 made of glass is hard to receive an influence of moisture or the like, and therefore reliability is high.

Modifications of the First Embodiment

Next, optical modules 1A and 1B according to a modification of the first embodiment will be described. The optical modules 1A and 1B are similar to the optical module 1 and have the same effect as the effect of the optical module 1. Therefore, components having the same function are denoted by the same reference numerals and descriptions are omitted.

Modification 1 of the First Embodimen

Figure 11:
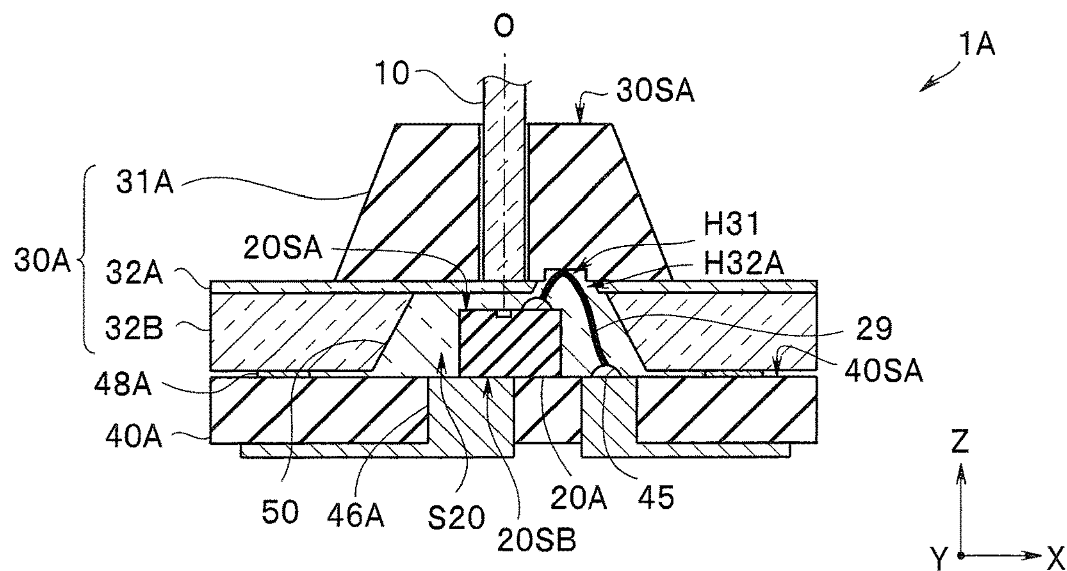
FIG. 11 is a cross-sectional view of an optical module according to a modification 1 of the first embodiment.

As shown in FIG. 11, in the optical module 1A according to a modification 1, a ferrule 31A has a tapered shape in which an area of the first principal plane 30SA is narrower than an area of the bottom surface. Thereby, laser light irradiated from above through the transparent containers 32A and 32B is not intercepted by the ferrule 31A. In the optical module 1A, the glass frit 48A can be arranged on the side inner than the glass frit 48G of the optical module 1. Therefore, the optical module 1A can cause a size (outer size) when planarly viewed from an optical axis orthogonal direction to be smaller than a size of the optical module 1.

Further, a ferrule recess H31 that communicates with the wire recess H32A is present in the ferrule 31A and a part of the bonding wire 29 is stored also in the ferrule recess H31.

Therefore, even if the bonding wire 29 is deformed into a convex shape above, it is easier to further reduce the height of the optical module 1A, than the optical module 1.

Note that, in an optical element 20A, an external electrode (not shown) is present on a rear surface 20SB on the opposite side to the light emitting surface 20SA and is directly bonded to an electrode on the third principal plane 40SA of a sealing plate 40A. Note that a bonding material 48A is made of laser-melted glass and may be further made of solder.

Modification 2 of the First Embodiment

Figure 12:
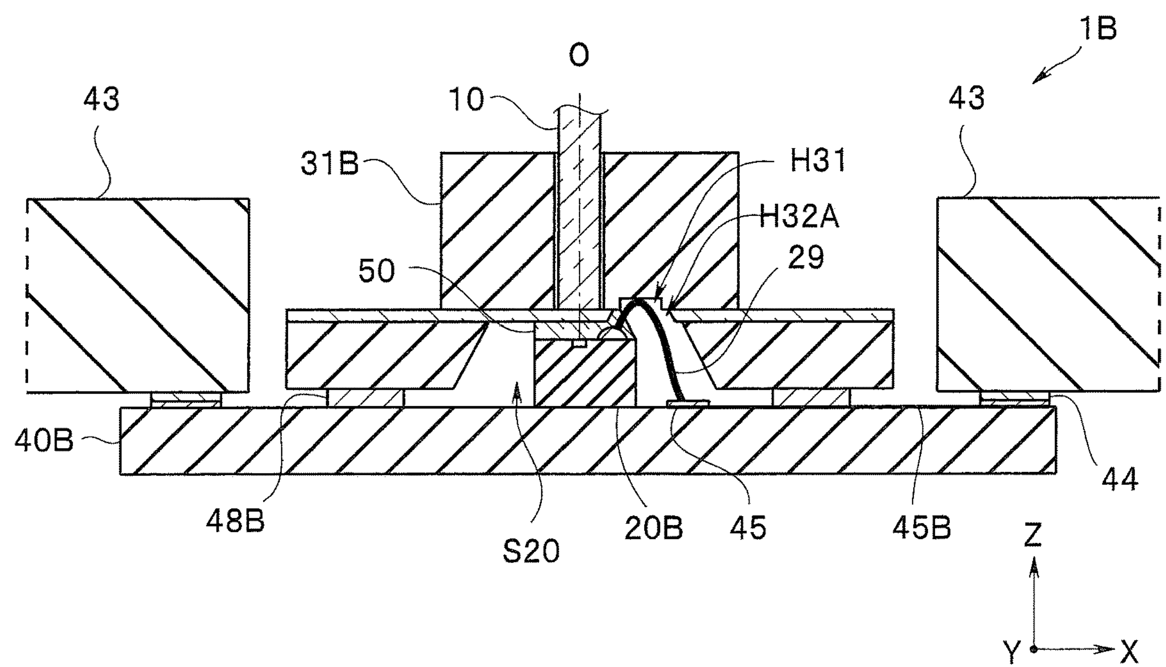
FIG. 12 is a cross-sectional view of an optical module according to a modification 2 of the first embodiment.

As shown in FIG. 12, in an optical module 1B according to a modification 2, a wiring board 43 is further bonded to a sealing plate 40B. Further, a ferrule 31B is a rectangular parallelepiped having the ferrule recess H31.

Further, the optical module 1B includes two external terminals 22 and two bonding electrodes 45 in a depth direction (Y axis direction) of paper sheet in the drawing and the two external terminals or the two bonding electrodes respectively are connected by the bonding wire 29. The two bonding electrodes 45 are electrically connected to a wiring 45B on the sealing plate 40B and further is electrically connected to the wiring board 43. Further, the transparent resin 50 is arranged centering an optical path of optical signals; however, the space S20 is not filled with the transparent resin 50.

As described above, configurations of the optical element, the ferrule, and the sealing plate can be arbitrarily changed according to specifications of the optical module.

Second Embodiment

Next, an optical module 1C according to a second embodiment will be described. The optical module 1C is similar to the optical module 1 or the like and has the same effect as the effect of the optical module 1 or the like. Therefore, components having the same function are denoted by the same reference numerals and descriptions are omitted.

Figure 13:
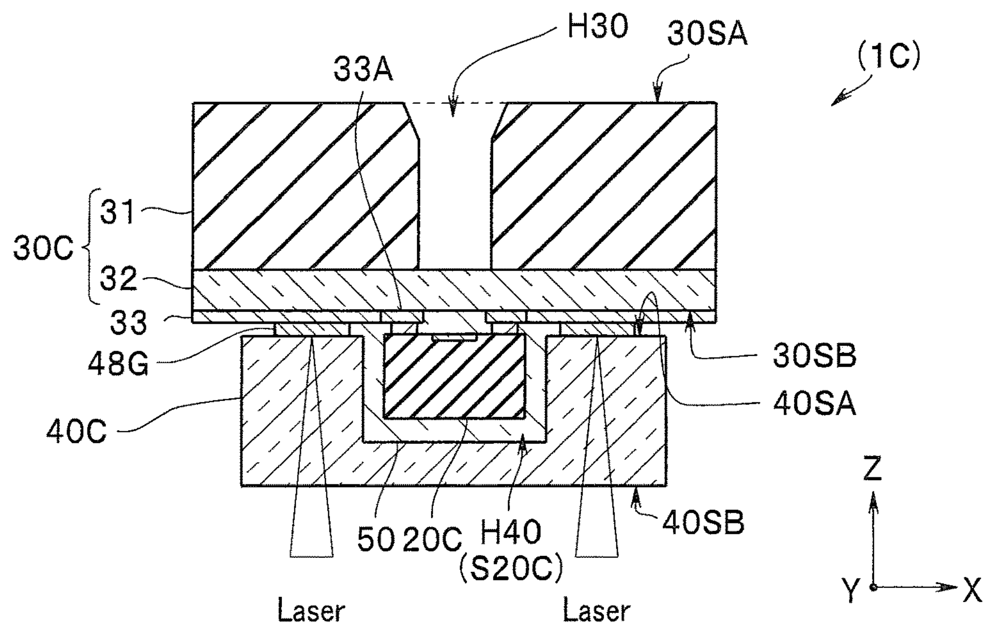
FIG. 13 is a cross-sectional view describing a manufacturing method for an optical module according to a second embodiment.

As shown in FIG. 13, in the optical module 1C, the external terminal 22 of an optical element 20C is directly bonded to a bonding electrode 33A on the second principal plane 30SB of a housing 30C, for example, by using an ultrasound bonding method. The bonding electrode 33A is arranged in an inner peripheral region surrounded by the annular bonding material 48 (48G) and has a wiring pattern 33 extended up to a periphery (outer side) of the bonding material 48. Two wiring patterns 33 intersect with the bonding material 48; however, since the bonding material 48 is made of glass of insulation materials, the two wiring patterns 33 are not shorted.

A space S20C in which the optical element 20C is stored is configured by a lower recess H40 in which an opening is present in the third principal plane 40SA of a sealing plate 40C.

The glass frit 48G is heated by laser light incident from the fourth principal plane 40SB of the sealing plate 40C made of a transparent material, for example, glass. A melting point of the sealing plate 40C is higher than a melting point of the bonding material 48.

In other words, a component that is an optical path of laser light is configured by materials having a melting point higher than a melting point of a bonding material.

Modifications of the Second Embodiment

Next, optical modules 1D to 1F according to a modification of the second embodiment will be described. The optical modules 1D to 1F are similar to the optical module 1C and have the same effect as the effect of the optical module 1C. Therefore, components having the same function are denoted by the same reference numerals and descriptions are omitted.

Modification 1 of the Second Embodiment

Figure 14:
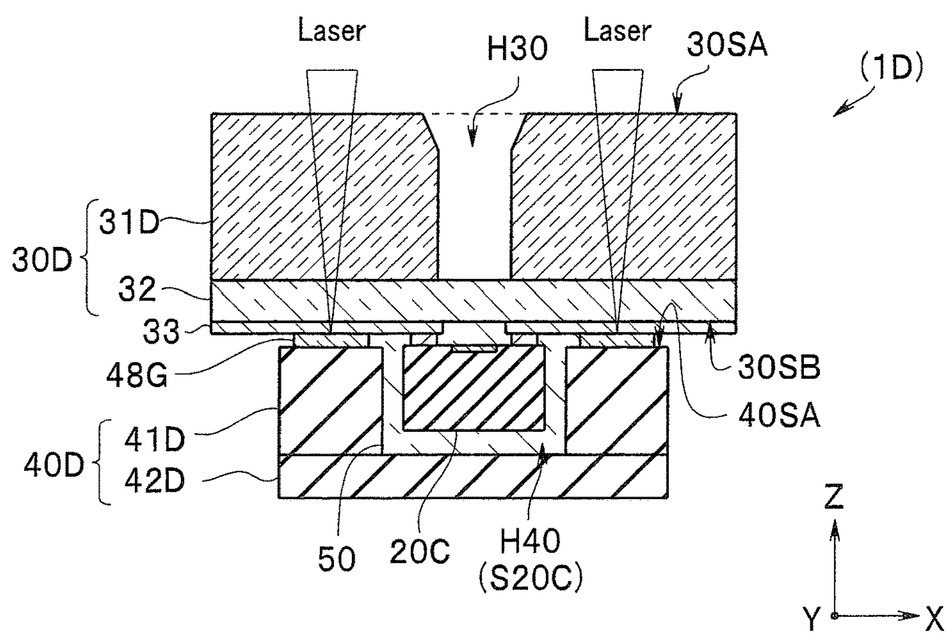
FIG. 14 is a top view of a connection wiring of an optical module according to a modification 1 of the second embodiment.

As shown in FIG. 14, in an optical module 1D according to a modification 1, a sealing plate 40D includes a frame portion 41D configuring a wall surface of the space S20 and a lid portion 42D configuring the fourth principal plane.

On the other hand, a ferrule 31D of a housing 30D has the same plan view dimension as the plan view dimension of the transparent container 32 and is made of a transparent material. Further, laser light for melting the bonding material 48 is incident from the first principal plane 30SA of the housing 30D. The housing 30D that is an optical path of laser light is configured by transparent materials having a melting point higher than a melting point of the bonding material 48 (48G).

Figure 15:
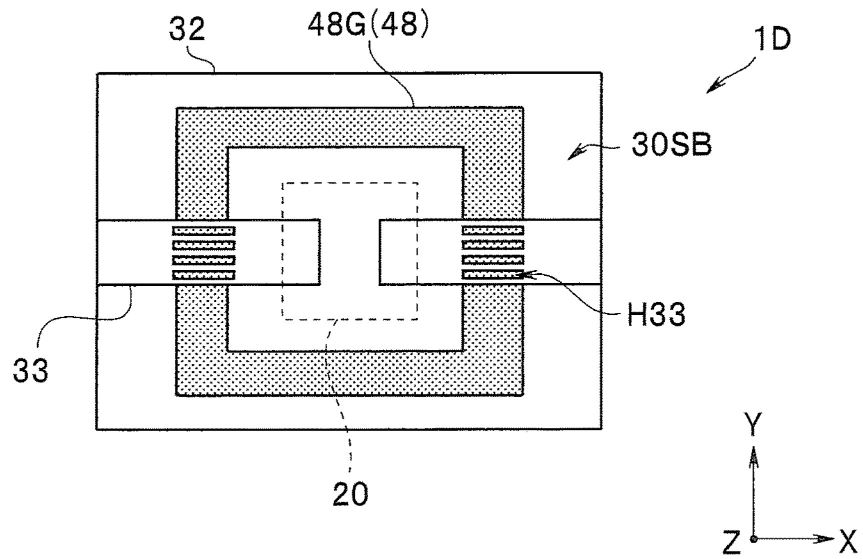
FIG. 15 is a cross-sectional view describing a manufacturing method for an optical module according to a modification 2 of the second embodiment.

Note that, as shown in FIG. 15, an opening H33 is present in a region in which the bonding material 48 of the wiring pattern 33 is arranged. Therefore, laser light incident from the first principal plane 30SA is irradiated to the glass frit 48G via the opening H33 in the wiring pattern 33.

The opening H33 is a slit in which an electric resistance of the wiring pattern 33 is not largely increased and that is formed to efficiently irradiate laser light, an opening patterned into a circular form etc., or an opening having a mesh structure.

Modification 2 of the Second Embodiment

Figure 16:
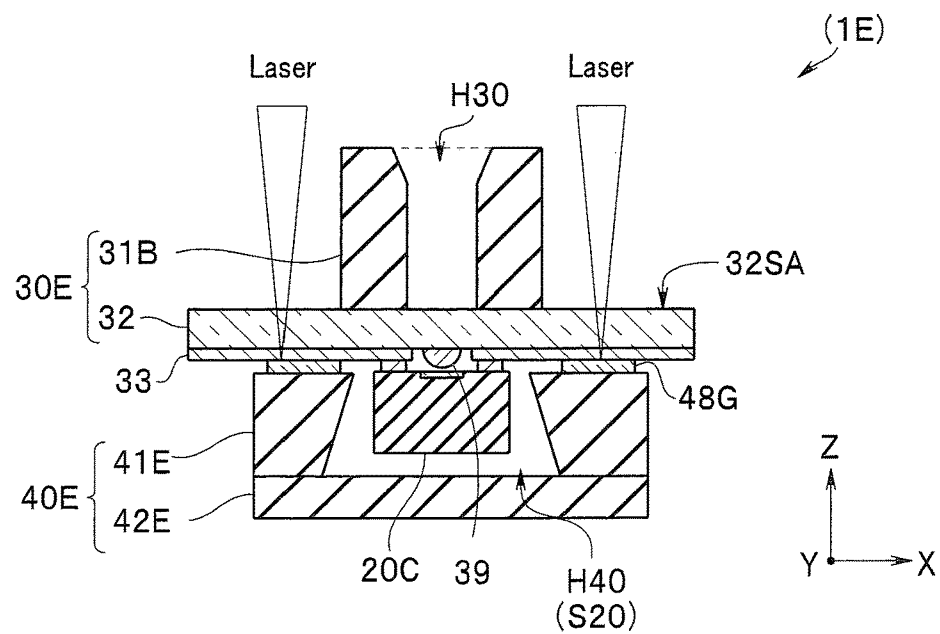
FIG. 16 is a cross-sectional view describing a manufacturing method for an optical module according to a modification 3 of the second embodiment.

As shown in FIG. 16, in an optical module 1E according to a modification 2 of the second embodiment, the space S20 is not filled with transparent resins. On the other hand, a lens 39 made of resins is arranged on the second principal plane 30SB of a housing 30E. Note that, in the optical module 1E, the optical element 20C may be connected to the wiring pattern 33 by using a bonding wire. Since a distance from the light emitting surface 20SA to the second principal plane 30SB becomes long, a configuration in which a connection is performed by using the bonding wire is larger, in an effect of using the lens 39, than a configuration in which a bonding is performed by using a bump.

An optical signal is efficiently incident on the optical fiber 10 via the lens 39 that is arranged in a state of facing the light emitting circuit 21 of the optical element.

Further, a sealing plate 40E includes a frame portion 41E and a lid portion 42E. The lower recess H40 in the frame portion 41E is inclined in a state in which a cross section of the space decreases in size while a wall surface goes in a direction (upper direction) toward the optical fiber. Therefore, it is easy to insert the optical element 20C into the space S20. Further, when a gelatinous glass frit is coated, an excessive glass frit flows along an inclined surface. Therefore, the inclined frame portion 41E does not disturb an optical element sealing process and has high productivity.

Modification 3 of the Second Embodiment

Figure 17:
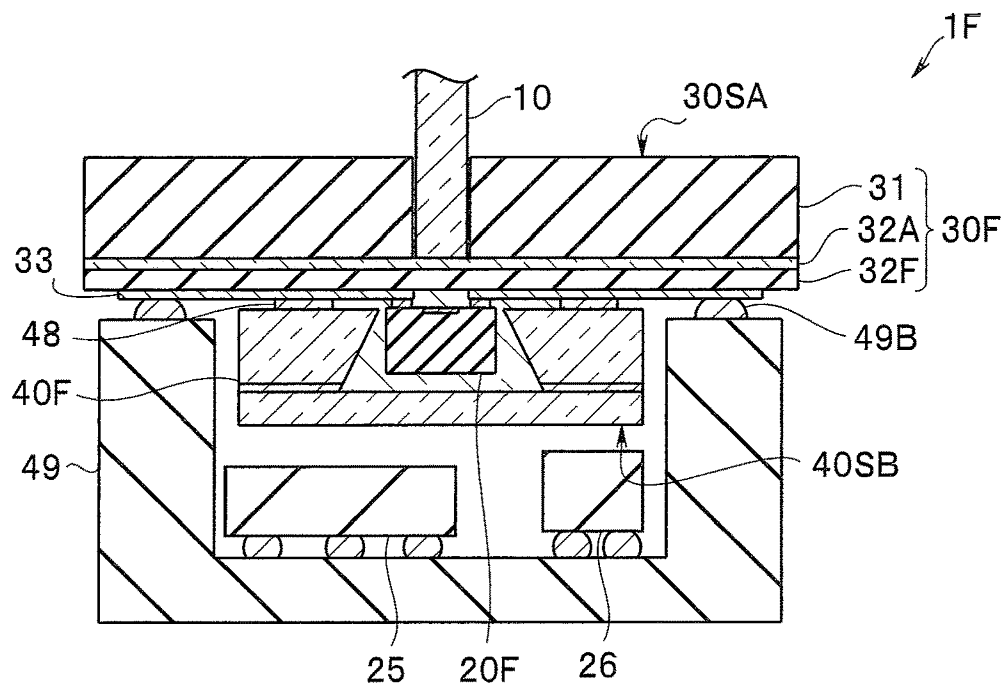
FIG. 17 is a cross-sectional view of the optical module according to the modification 3 of the second embodiment.

As shown in FIG. 17, in an optical module 1F according to a modification 3 of the second embodiment, an optical element 20F generates infrared light having a wavelength of 1300 to 1600 nm. A housing 30F is manufactured from an SOI wafer. More specifically, from the first principal plane 30SA of the SOI wafer including a silicon layer 31/an oxide silicon layer 32A/a silicon layer 32F, the insertion hole H30 is formed by using the oxide silicon layer 32A as the etching stop layer. The bottom surface of the insertion hole H30 is made of the oxide silicon layer 32A and further the silicon layer 32F is present on the optical path. However, the silicon layer 32F is substantially made of a transparent material with respect to infrared light and therefore the transmission efficiency of the silicon layer 32F is not reduced.

In a sealing plate 40F of the optical module 1F, a frame portion and a lid portion are bonded by using an annular bonding material made of glass. The bonding material 48 is melted by laser irradiation from the fourth principal plane 40SB.

Further, an electrode 49B on a wiring board 49 on which electronic components 25 and 26 are mounted is bonded to the wiring pattern 33 in the housing 30F. For example, the electronic component 25 is a drive IC that outputs a driving signal to the optical element 20F and the electronic component 26 is a chip capacitor.

Note that it goes without saying that, like the optical module 1F, also the optical modules 1 (1A to 1E) may be bonded to the wiring board on which electronic components are mounted.

Third Embodiment

Figure 18:
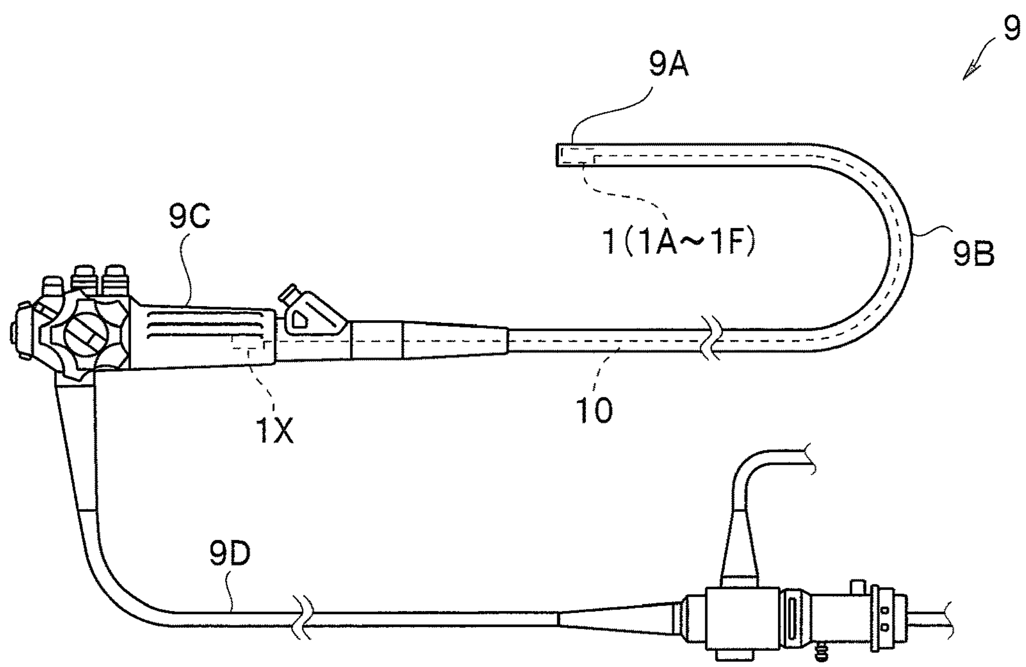
FIG. 18 is an outline view of an endoscope according to a third embodiment.

Next, an endoscope 9 according to a third embodiment will be described. As shown in FIG. 18, the endoscope 9 includes the optical module 1 (1A to 1F) at a distal end portion 9A of an insertion portion 9B.

The endoscope 9 includes the insertion portion 9B in which an image pickup portion including an image pickup device having a large number of pixels is arranged at the distal end portion 9A, an operation portion 9C that is arranged on a proximal end side of the insertion portion 9B, and a universal code 9D that is extended from the operation portion 9C.

An electric signal outputted by the image pickup portion is converted into an optical signal by an E/O-type optical module 1 (1A to 1F). Further, the optical signal through the optical fiber 10 is converted into an electric signal again by an O/E-type optical module 1X in which an optical element that is arranged at the operation portion 9C is a photodiode and the electric signal is transmitted through a metal wiring. In other words, a signal is transmitted through the optical fiber 10 in the insertion portion 9B having a small diameter.

Alternatively, the electric signal outputted by the image pickup portion may be transmitted as an electric signal through the insertion portion 9B. Further, the electric signal may be converted to an optical signal by an E/O-type optical module 1 (1A to 1F) that is arranged in the operation portion 9C and converted to an electric signal by the O/E-type optical module 1X in which the optical element arranged at a main body (not shown) is a photodiode.

Alternatively, the electric signal outputted by the image pickup portion may be converted to an optical signal by the E/O-type optical module 1 (1A to 1F). Further, the optical signal may be transmitted via the insertion portion 9B, the operation portion 9C, and the universal code 9D through the optical fiber 10 and converted to an electric signal by the O/E-type optical module 1X in which the optical element arranged in the main body (not shown) is a photodiode.

As described above already, the optical module 1 (1A to 1F) is small and has high reliability and productivity. Therefore, the insertion portion of the endoscope 9 has a small diameter and the endoscope 9 has high reliability and productivity.

Note that the optical module 1X is arranged in the operation portion 9C in which an arrangement space is relatively wide and desirably has the same configuration as the configuration of the optical module 1 or the like of the present invention. Further, the endoscope 9 is a flexible endoscope and further may be a rigid endoscope. Further, a control signal to the image pickup portion may be converted to an optical signal by the optical module 1 (1A to 1F) arranged in the operation portion 9C. Further, the optical signal may be converted to an electric signal by the optical module 1X arranged at the distal end portion 9A.

Note that, in the optical module 1 or the like, the optical element 20 is a light emitting element. On the other hand, even if the optical element of the optical module is a light receiving element such as a photodiode, which has a light receiving portion that is a light receiving circuit in which an optical signal is inputted, the optical element has the same effect as the effect of the optical module 1 or the like.

In other words, the optical element just has to include a light emitting circuit that outputs an optical signal or a light receiving circuit in which an optical signal is inputted, and an external terminal connected to the light emitting circuit or the light receiving circuit.

The present invention is not limited to the embodiments described above, and various changes, combinations, and modifications may be made without departing from the spirit of the present invention.

What is claimed is:

1. An optical module for endoscope comprising:

an optical element including a light emitting circuit configured to output an optical signal or a light receiving circuit to which the optical signal is inputted and an external terminal connected to the light emitting circuit or the light receiving circuit;

a housing including a first principal plane and a second principal plane on an opposite side to the first principal plane, an insertion hole into which an optical fiber configured to transmit the optical signal is inserted being present, and an opening of the insertion hole that has a bottom and a bottom surface of which is made of a transparent material being present in the first principal plane; and a sealing plate including a third principal plane and a fourth principal plane on the opposite side to the third principal plane, the third principal plane being bonded to the second principal plane of the housing using an annular bonding material; wherein the optical element is stored in a space configured by an upper recess in which an opening is present in the second principal plane of the housing, and the optical element is arranged in the third principal plane, the external terminal and a bonding electrode in the third principal plane are connected using a bonding wire, and a wire recess in which a part of the bonding wire is stored is present in a bottom surface of the upper recess.

2. The optical module for endoscope according to claim 1, wherein the bonding material is made of glass formed by heating glass frit by laser light irradiation.

3. The optical module for endoscope according to claim 1, wherein

A wall surface of the space is inclined in a state in which a cross section of the space decreases in size in a direction toward the insertion hole.

4. The optical module for endoscope according to claim 1, wherein at least any one of the housing and the sealing plate is made of a transparent material having a melting point higher than a melting point of the bonding material.

5. The optical module for endoscope according to claim 4, wherein the housing includes a ferrule in which a through hole configuring the insertion hole is present, and a transparent container made of a transparent material having a melting point higher than a melting point of the bonding material, which configures the bottom surface and the second principal plane.

6. The optical module for endoscope according to claim 5, wherein the ferrule is made of silicon and the bonding material is located around the ferrule in plan view in a direction of the first principal plane.

7. The optical module for endoscope according to claim 1, wherein the space is filled with a transparent resin.

8. An endoscope comprising:

an optical module for endoscope, wherein the optical module for endoscope includes:

an optical element including a light emitting circuit configured to output an optical signal or a light receiving circuit to which the optical signal is inputted and an external terminal connected to the light emitting circuit or the light receiving circuit;

a housing including a first principal plane and a second principal plane on an opposite side to the first principal plane, an insertion hole into which an optical fiber configured to transmit the optical signal is inserted being present, and an opening of the insertion hole that has a bottom and a bottom surface of which is made of a transparent material being present in the first principal plane; and a sealing plate including a third principal plane and a fourth principal plane on the opposite side to the third principal plane, the third principal plane being bonded to the second principal plane of the housing using an annular bonding material, wherein the optical element is stored in a space configured by an upper recess in which an opening is present in the second principal plane of the housing, and the optical element is arranged in the third principal plane, the external terminal and a bonding electrode in the third principal plane are connected using a bonding wire, and a wire recess in which a part of the bonding wire is stored is present in a bottom surface of the upper recess.

9. A manufacturing method for an optical module for endoscope, comprising:

bonding a first transparent wafer in which a wire recess is formed and a second transparent wafer in which a container recess is formed in a state in which the wire recess and the container recess are overlapped and manufacturing a bonding transparent wafer including an upper recess including the wire recess and the container recess;

processing the first transparent wafer of the bonding transparent wafer into a thin layer;

bonding a silicon wafer to the first transparent wafer of the bonding transparent wafer and manufacturing a bonding wafer;

forming, by etching, an insertion hole in which an optical fiber is inserted into the silicon wafer of the bonding wafer;

manufacturing a housing by cutting the bonding wafer;

arranging, at a sealing plate, an optical element including a light emitting circuit configured to output an optical signal or a light receiving circuit in which the optical signal is inputted and an external terminal connected to the light emitting circuit or the light receiving circuit, and connecting the external terminal and a bonding electrode using a bonding wire;

injecting a transparent resin into the upper recess;

arranging glass frit that is a bonding material between the bonding wafer and the sealing plate in a state in which a part of the bonding wire is stored in the wire recess; and irradiating laser light onto the glass frit and bonding the bonding wafer and the sealing plate.

10. The manufacturing method for an optical module for endoscope according to claim 9, wherein A wall surface of a space is inclined in a state in which a cross section of the space decreases in size in a direction toward the insertion hole.

11. The manufacturing method for an optical module for endoscope according to claim 9, wherein at least any one of the housing and the sealing plate is made of a transparent material having a melting point higher than a melting point of the bonding material.

* * * * *